(12) United States Patent
Bihary et al.

(10) Patent No.: US 7,670,344 B2
(45) Date of Patent: Mar. 2, 2010

(54) FINELY ADJUSTABLE RESECTION ASSEMBLY

(75) Inventors: Diane L. Bihary, Flat Rock, MI (US); Troy D. Martin, Pierceton, IN (US)

(73) Assignee: Depuy Products, Inc., Warsaw, IN (US)

( * ) Notice: Subject to any disclaimer, the term of this patent is extended or adjusted under 35 U.S.C. 154(b) by 424 days.

(21) Appl. No.: 11/410,404

(22) Filed: Apr. 25, 2006

(65) Prior Publication Data

US 2006/0247646 A1    Nov. 2, 2006

Related U.S. Application Data

(60) Provisional application No. 60/676,205, filed on Apr. 28, 2005.

(51) Int. Cl.
*A61F 5/00* (2006.01)
(52) U.S. Cl. ...................................................... 606/87
(58) Field of Classification Search .................. 606/79, 606/83, 86, 87, 88
See application file for complete search history.

(56) References Cited

U.S. PATENT DOCUMENTS

| | | | |
|---|---|---|---|
| 4,952,213 A | * | 8/1990 | Bowman et al. ............... 606/79 |
| 5,306,276 A | | 4/1994 | Johnson et al. |
| 5,451,228 A | | 9/1995 | Johnson et al. |
| 5,514,143 A | | 5/1996 | Bonutti et al. |
| 5,562,674 A | * | 10/1996 | Stalcup et al. ................ 606/88 |
| 5,658,293 A | * | 8/1997 | Vanlaningham ............... 606/88 |
| 5,681,316 A | | 10/1997 | Deorio et al. |
| 6,090,114 A | * | 7/2000 | Matsuno et al. ............... 606/88 |

* cited by examiner

*Primary Examiner*—Eduardo C Robert
*Assistant Examiner*—Elana B Fisher
(74) *Attorney, Agent, or Firm*—Stephen J. Manich

(57) ABSTRACT

A finely-adjustable resection guide has two bodies pivotally connected to each other. One of the bodies has a plurality of threaded through-bores extending in perpendicular directions through the body. Two thumbscrews extend through the threaded through-bores. The thumbscrews can translate linearly with respect to the body as they are turned. A cutting block is pivotally connected to the body that has the thumbscrews. Linear translation of one of the thumbscrews causes the cutting guide surface of the cutting block to pivot about one axis and linear translation of the other thumbscrew causes the cutting guide surface to pivot about another axis that is perpendicular to the first axis. A third threaded member is provided to adjust the proximal-distal position of the cutting guide surface.

14 Claims, 13 Drawing Sheets

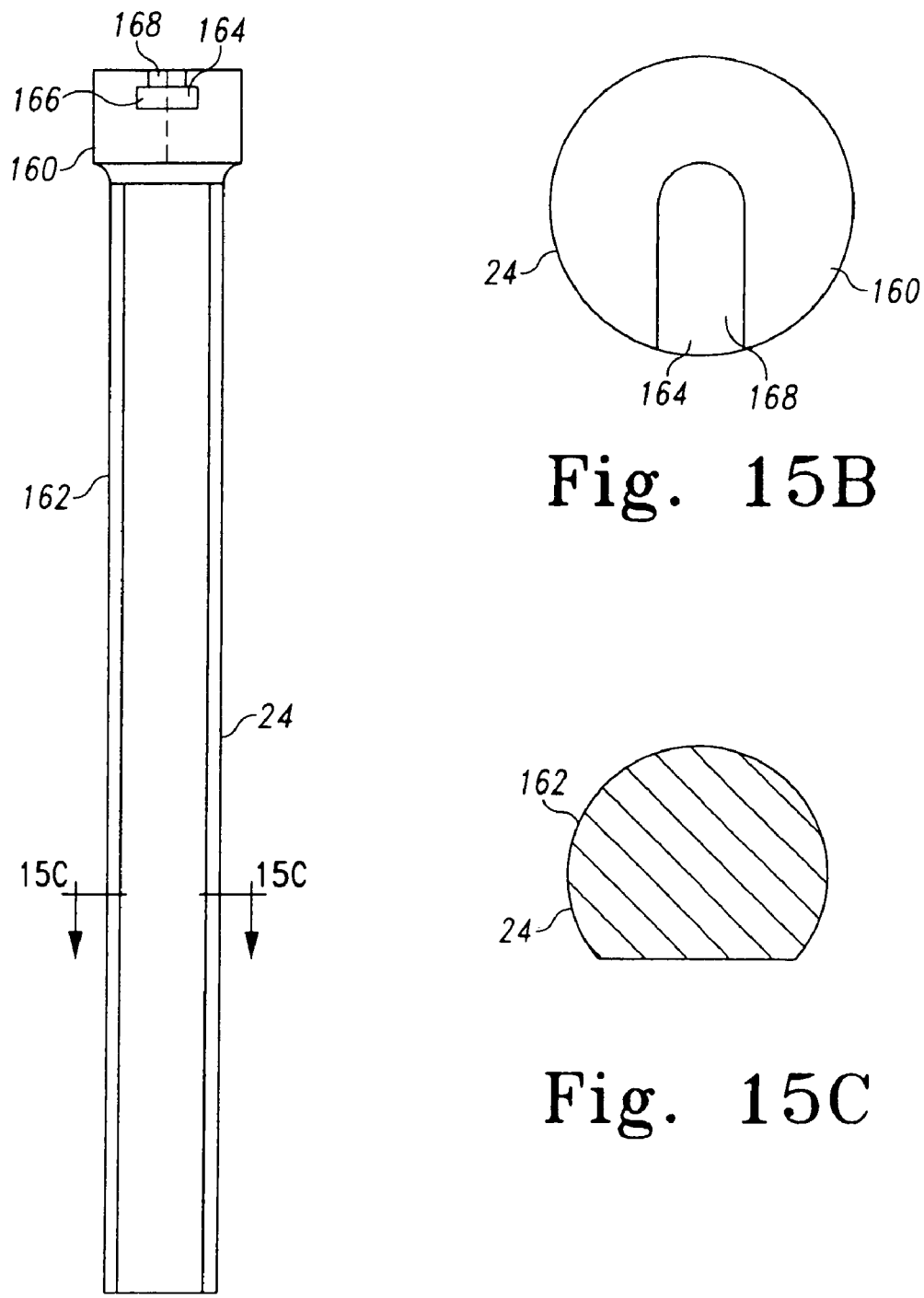

FINELY ADJUSTABLE RESECTION ASSEMBLY

CROSS-REFERENCE TO RELATED APPLICATIONS

This application claims priority to U.S. Provisional Application Ser. No. 60/676,205, entitled FINELY ADJUSTABLE TIBIAL RESECTION ASSEMBLY, filed Apr. 28, 2005, which is herein incorporated by reference in its entirety for all purposes.

BACKGROUND OF THE INVENTION

The present invention relates to devices used to prepare a bone to receive a prosthetic implant, and more particularly, to such a device used to prepare the proximal tibia to receive a proximal tibial implant.

The knee joint basically consists of the bone interface of the distal end of the femur and the proximal end of the tibia. Appearing to cover or at least partially protect this interface is the patella which is a sesamoid bone within the tendon of the long muscle (quadriceps) on the front of the thigh. This tendon inserts into the tibial tuberosity and the posterior surface of the patella is smooth and glides over the femur.

The femur is configured with two knob like processes (the medial condyle and the lateral condyle) which are substantially smooth and articulate with the medial plateau and the lateral plateau of the tibia, respectively. The plateaus of the tibia are substantially smooth and slightly cupped thereby providing a slight receptacle for receipt of the femoral condyles.

When the knee joint is injured whether as a result of an accident or illness, a prosthetic replacement of the damaged joint may be necessary to relieve pain and to restore normal use to the joint. Typically the entire knee joint is replaced by means of a surgical procedure that involves removal of the ends of the corresponding damaged bones and replacement of these ends with prosthetic implants. This replacement of a native joint with a prosthetic joint is referred to as a primary total-knee arthroplasty.

The surgical preparation of the patella, tibia and femur during primary total-knee arthroplasty is a complex procedure. A number of bone cuts are made to effect the placement and orientation of the prosthetic components on the bones with the appropriate joint gaps in extension and flexion. To resect the tibia, a cutting guide or block is mounted on the proximal tibia. The position, alignment and orientation of the cutting block are important for optimal performance of the prosthetic implant components. Generally, the tibial cutting block is positioned, aligned and oriented so that the cutting guide surface is in the optimal proximal-distal position, posterior slope, and varus-valgus orientation. A variety of alignment guides and cutting blocks have been provided in the prior art for use in preparing bone surfaces in primary total-knee arthroplasty, including alignment guides and cutting blocks used in preparing the proximal tibia.

Prior art alignment guides include the Specialist® 2 instruments (DePuy Orthopaedics, Inc., Warsaw, Ind.) for use with DePuy Orthopaedics' P.F.C.® Sigma Knee System. The tibial alignment guide for this instrument system includes an ankle clamp, a pair of telescoping alignment rods and a cutting block. Parts of this system are manually adjustable: the proximal-distal position of the cutting block is adjusted by sliding the telescoping rods and then locking the rods in the desired position; posterior slope is set at the ankle by sliding the distal end of the alignment rod in an anterior-posterior direction to thereby pivot the cutting block into the desired orientation; varus-valgus slope is set by pivoting the cutting block so that the alignment guide pivots about a rod at the ankle clamp. U.S. Pat. No. 6,090,114 discloses a tibial plateau resection guide. This system also uses an ankle clamp and extension rods to set the position and orientation of the cutting block. U.S. Pat. No. 5,451,228 also utilizes an ankle clamp but allows for angular orientation in the anterior-posterior plane to predetermined angular orientations using a thumb actuated slide mechanism; the device is however limited to predetermined angular settings. U.S. Pat. Nos. 6,685,711 and 6,595,997 disclose an apparatus and method for resecting bone that provides for aligning a resection guide in three degrees of freedom.

SUMMARY OF THE INVENTION

The present invention provides a resection assembly that allows for fine adjustments of the cutting block position after a preliminary position is set. With the assembly of the present invention, these fine adjustments can be made through controlled movements through a wide range of distances and angles.

In one aspect, the present invention provides these advantages by providing a finely-adjustable resection guide assembly that comprises a first body, a second body, a first threaded member, a second threaded member, a third threaded member and a cutting block. The second body has anterior and posterior surfaces and a plurality of through-bores extending through the second body from the anterior to the posterior surfaces. The second body is pivotally connected to the first body for relative pivotal movement about a first axis. The first threaded member extends through the first body in a first direction and is capable of linear translation with respect to the first body in the first direction. The second threaded member extends through the first body in a second direction and is capable of linear translation with respect to the first body in the second direction. The third threaded member extends through the second body in a third direction and is capable of linear translation with respect to the second body in the third direction. The cutting block has a cutting guide surface, and is pivotally connected to the first body. Linear translation of the first threaded member causes pivotal movement of the cutting block about the second axis. Linear translation of the second threaded member causes pivotal movement of the cutting block about the first axis. Linear translation of the third threaded member changes the distance between the second body and the cutting surface of the cutting block.

In another aspect, the present invention provides these advantages by providing a finely-adjustable tibial resection assembly that comprises a cutting block, a varus-valgus adjustment plate, a transition block, a proximal screw, a distal screw, a posterior slope adjustment plate, a pin block and an adjustment rod. The cutting block has a cutting guide surface. The varus-valgus adjustment plate extends distally from the cutting block, and has a distal tang. The transition block has spaced proximal end walls defining a proximal channel and spaced distal end walls defining a distal channel. The proximal channel extends in a medial-lateral direction and the distal channel extends in an anterior-posterior direction. The transition block also has a proximal threaded bore extending in a medial-lateral direction and a distal threaded bore extending in an anterior-posterior direction. The proximal screw extends through the proximal threaded bore of the transition block. The proximal screw has a circumferential groove. The distal screw extends through the distal threaded bore of the transition block. The distal screw has a circumferential groove. The posterior slope adjustment plate has a proximal tang. The pin block has a plurality of through bores extending in the proximal-distal direction; at least one of the through bores is threaded. The pin block is positioned distal to the posterior slope adjustment plate. The adjustment rod has a threaded shaft engaging the threads of the threaded through bore in the pin block. The adjustment rod also includes a head and a proximal end in contact with the posterior slope adjustment plate. The distance between the pin block and the cutting guide surface can be adjusted by turning the head of the adjustment rod. A portion of the varus-valgus plate is received in the proximal channel of the transition block and pivotally connected to the transition block so that the varus-valgus plate and the cutting block are capable of pivoting with respect to the transition block about an anterior-posterior axis. A portion of the posterior slope adjustment plate is received in the distal channel of the transition block and pivotally connected to the transition block so that the posterior slope adjustment plate is capable of pivoting with respect to the transition block about a medial-lateral axis. The distal tang of the varus-valgus plate is received in the circumferential groove of the proximal screw and the proximal tang of the posterior slope adjustment plate is received in the circumferential groove of the distal screw.

BRIEF DESCRIPTION OF THE DRAWINGS

The invention will be better understood by reference to the figures of the drawings wherein like numbers denote like parts throughout and wherein:

FIG. 15A is an elevation of the alignment rod of the tibial resection assembly of FIGS. 1-3;

FIG. 15B is an end view of the alignment rod of FIG. 15A, showing the proximal end of the rod;

FIG. 15C is a cross-section of the shaft of the alignment rod of FIGS. 15A-15B, taken along line 15C-15C of FIG. 15A;

DETAILED DESCRIPTION OF THE ILLUSTRATED EMBODIMENT

A finely adjustable tibial resection assembly embodying the principles of the present invention is illustrated at 10 in the accompanying figures. This assembly allows the surgeon the freedom to use the assembly with a standard ankle clamp if desired, as well as to use the assembly with a standard stylus assembly if desired. The assembly allows the surgeon to first set a preliminary position of the assembly and to fix the assembly in this preliminary position. After the surgeon has fixed the assembly in the preliminary position, the surgeon can make fine adjustments of the position and orientation of the cutting block by turning threaded elements. The use of these threaded elements to adjust position and orientation allows for finely controlled movements of the cutting block to a wide range of positions and orientations, resulting in a more accurate final position and orientation of the cutting block. The assembly can be used with commercially available computer imaging systems so that the finely controlled movements of the cutting block can be related to a computer image of the desired position and orientation of the cutting block. Once the cutting block is in the desired final position and orientation, standard pins can be set through the cutting block into the tibia to set the cutting block prior to resection.

Figure 1:
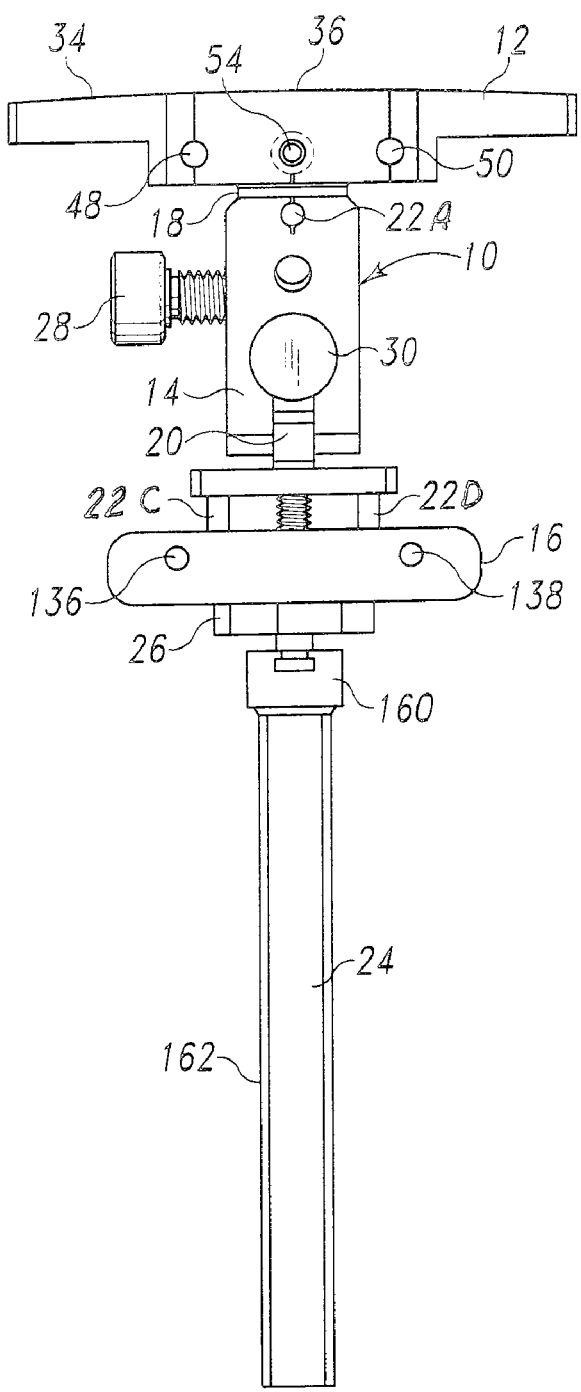
FIG. 1 is a front or anterior view of a finely adjustable tibial resection assembly of a cutting block and adjustable alignment system incorporating the principles of the present invention.
Figure 2:
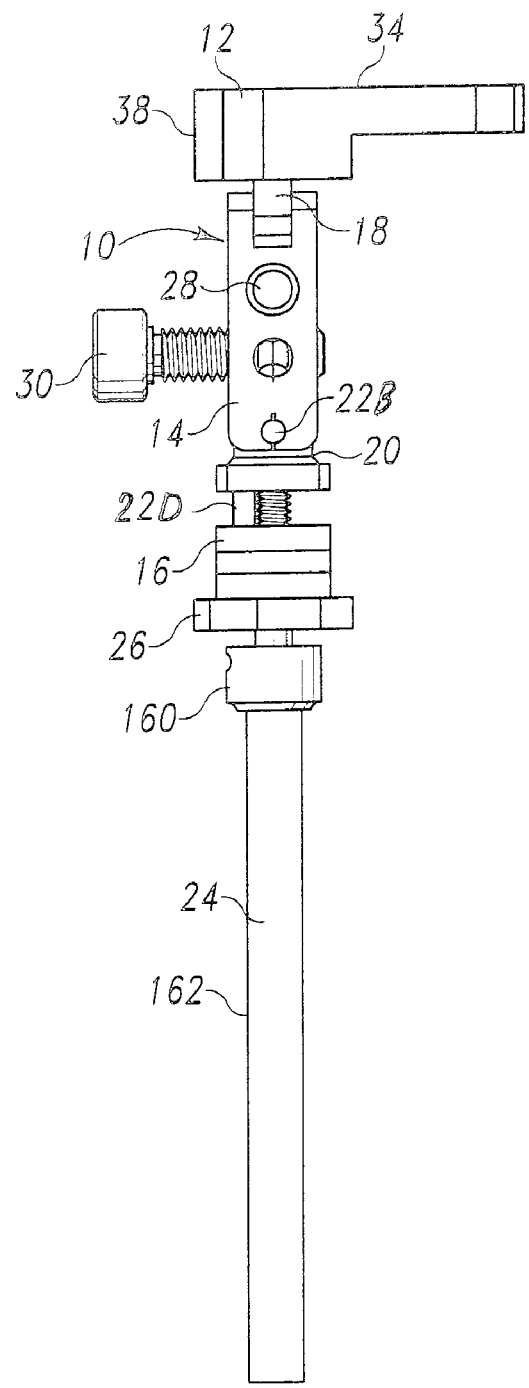
FIG. 2 is a side view of the tibial resection assembly of FIG. 1.
Figure 3:
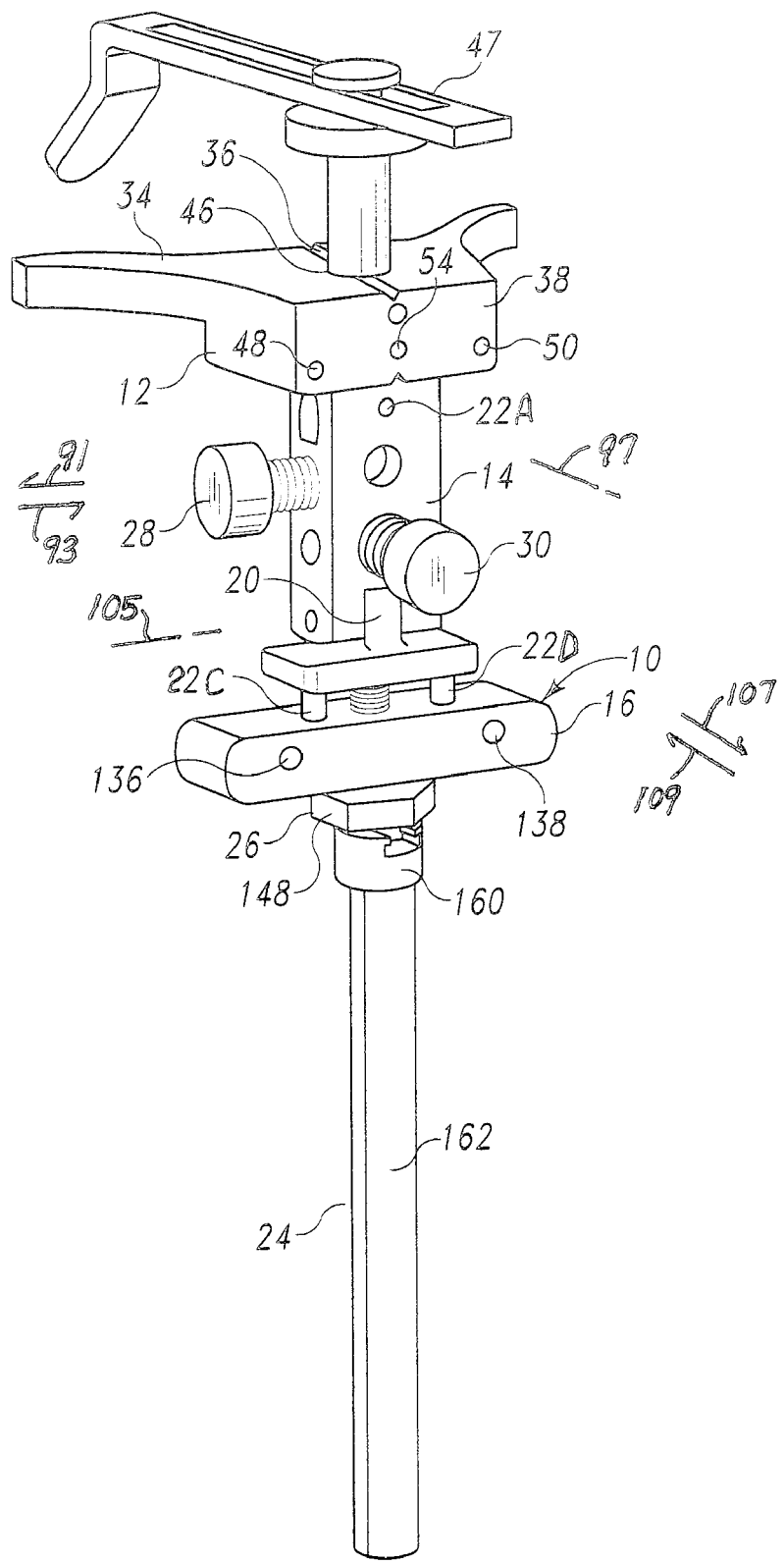
FIG. 3 is a perspective view of the tibial resection assembly of FIGS. 1-2.

As shown in FIGS. 1-3, the finely-adjustable tibial resection assembly 10 includes a plurality of parts: a top or proximal tibial cutting block 12; a first body or transition block 14; a second body or pin block 16; a varus-valgus adjustment plate 18; a posterior slope adjustment plate 20; a plurality of dowel pins 22A, 22B, 22C, 22D; an alignment rod 24; an adjustment rod 26; and a plurality of thumb screws 28, 30.

Figure 4A:
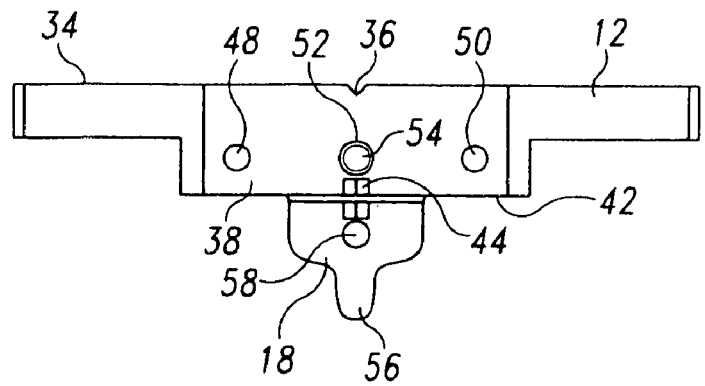
FIG. 4A is a front elevation, or anterior view, of the subassembly of a cutting block and varus-valgus adjustment plate of the tibial resection assembly of FIGS. 1-3.
Figure 4B:
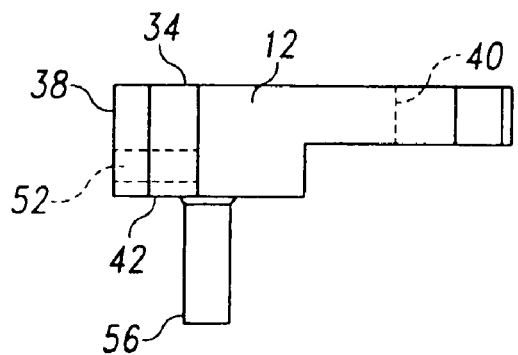
FIG. 4B is a side view, or medial view, of the subassembly of a cutting block and varus-valgus adjustment plate FIG. 4A.
Figure 4C:
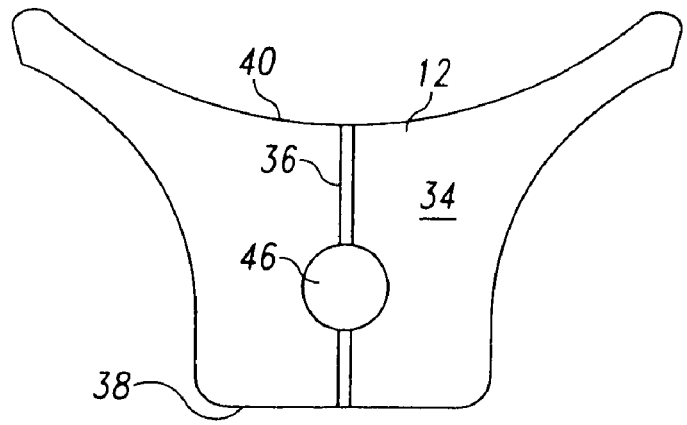
FIG. 4C is a top plan view of the subassembly of a cutting block and varus-valgus adjustment plate of FIGS. 4A and 4B, showing the proximal surface of the cutting block.

The top or proximal tibial cutting block 12 is illustrated in FIGS. 4A, 4B and 4C with an integral varus-valgus adjustment plate 18. In the illustrated embodiment, this cutting block 12 and proximal adjustment plate 18 comprise a single integral component, although it should be understood that these two parts 12, 18 could be made as a subassembly of separate components if desired.

The cutting block 12 includes a flat proximal cutting guide surface 34 with a v-shaped groove 36 extending from the anterior side 38 of the cutting block 12 to the posterior side 40 of the cutting block 12. The distal surface 42 of the cutting block 12 also has a v-shaped groove 44 extending in the anterior side 38 (see FIG. 4A). A proximal through bore 46 (shown in FIG. 4C) extends from the proximal cutting guide surface 34 to the distal surface 42 of the cutting block 12. As shown in FIG. 3, this proximal through bore 46 may receive a stylus assembly 47 for use in setting a preliminary position of the cutting block 12.

The cutting block 12 also includes two through bores 48, 50 extending from the anterior side 38 through the body of the cutting block to the posterior side 40. These through bores 48, 50 are provided to receive pins for fixing the cutting block to the proximal tibia when the cutting block is in the desired final position.

A central bore 52 in the anterior side 38 of the body of the cutting block 12 receives a ball plunger 54 that fixes the cutting block 12 to the stylus assembly 47.

The integral varus-valgus adjustment plate 18 extends distally from the distal surface 42 of the cutting block 12 to a distal tang 56 shown in FIGS. 4A and 4B. Between the distal tang 56 and the distal surface 42 of the cutting block 12, the varus-valgus adjustment plate 18 has a through bore 58 (shown in FIG. 4A) extending in an anterior-posterior direction. In the tibial resection assembly 10, the through bore 58 receives a dowel pin 22A to pivotally mount the integral varus-valgus adjustment plate 18 and cutting block 12 to the transition block 14.

The transition block 14 is illustrated in FIGS. 5A-5E. At the proximal end 60, the transition block 14 includes spaced end walls 62, 64 forming proximal through channel 66 extending from the medial side to the lateral side of the block 14. At the distal end 68, the transition block 14 includes spaced end walls 70, 72 forming a distal through channel 74 extending from the anterior side to the posterior side of the block 14.

Figure 5A:
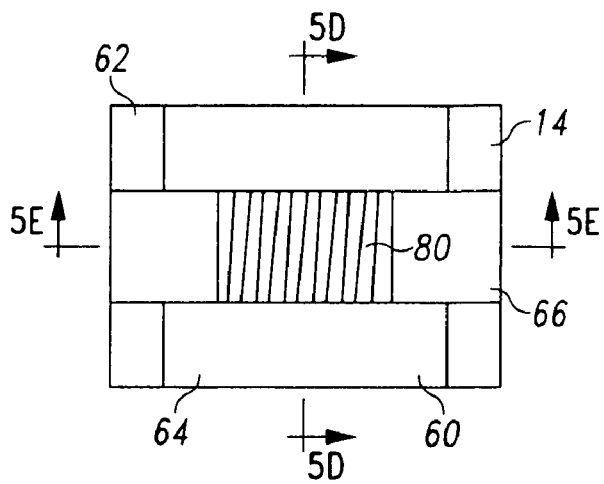
FIG. 5A is a top plan view of the transition block of the tibial resection assembly of FIGS. 1-3, showing the proximal end of the transition block.
Figure 5B:
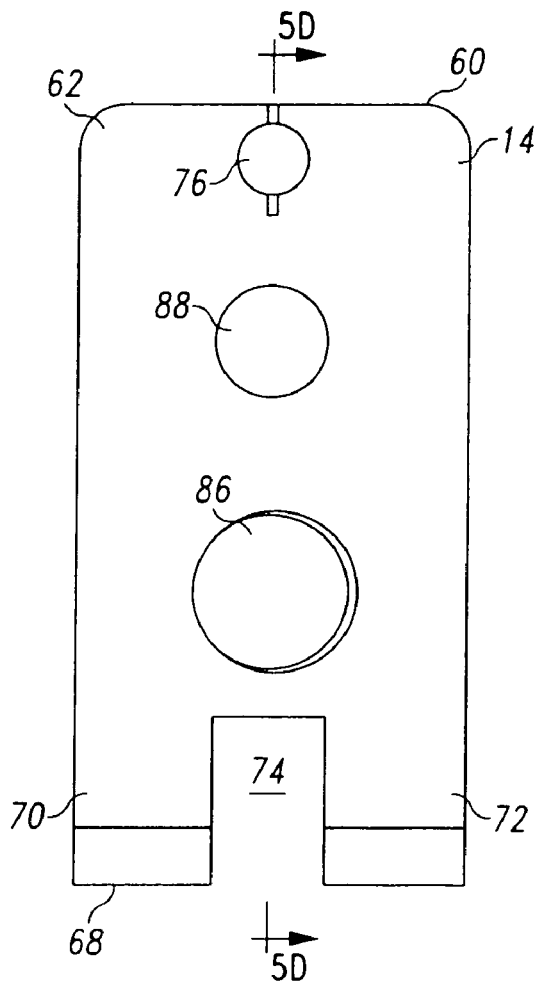
FIG. 5B is a front elevation, or anterior view, of the transition block of FIG. 5A.
Figure 5C:
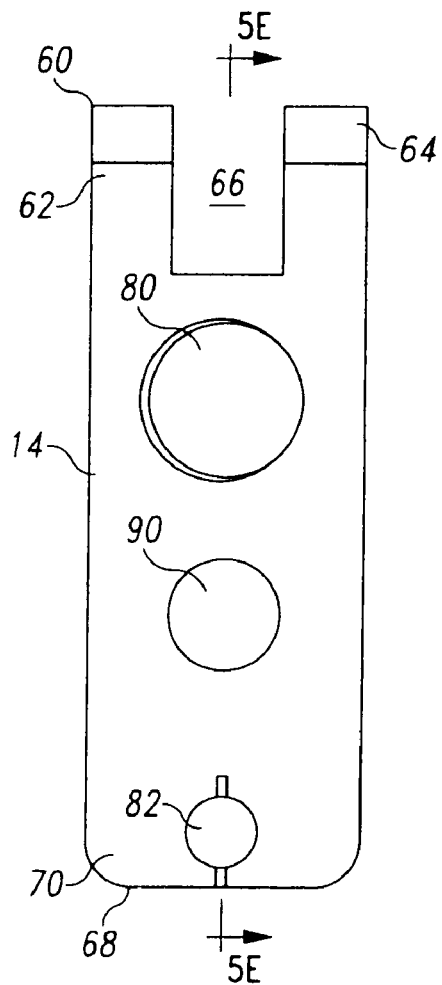
FIG. 5C is a side elevation, or medial view, of the transition block of FIGS. 5A-5B.
Figure 5D:
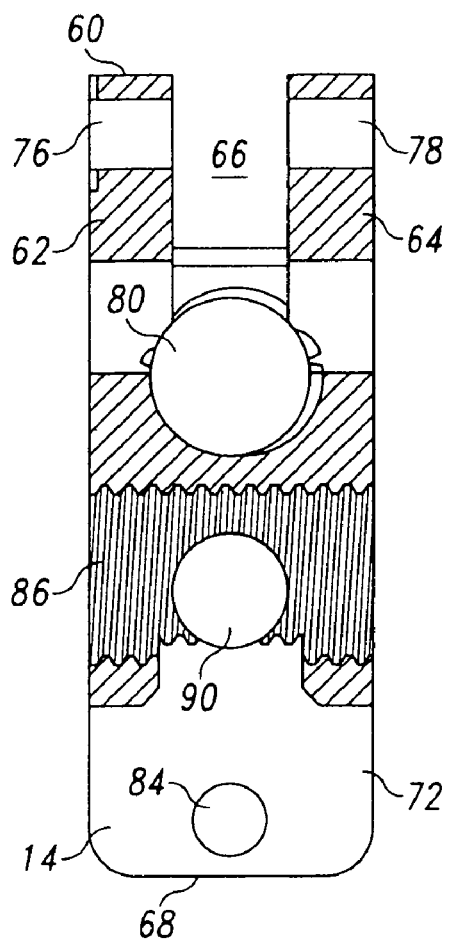
FIG. 5D is a cross-section of the transition block of FIGS. 5A-5C, taken along line 5D-5D of FIGS. 5A and 5B.

The transition block 14 also includes a plurality of through bores. As shown in FIG. 5D, a proximal pair of through bores 76, 78 extend through the walls 62, 64 in an anterior-posterior direction. The proximal through bores 76, 78 are co-axial, and intersect the proximal channel 66. A proximal threaded through bore 80 extends through the body of the transition block 14 in a medial-lateral direction. The central proximal portion of the threaded through bore 80 is exposed to the proximal channel 66, as shown in FIG. 5E.

Figure 5E:
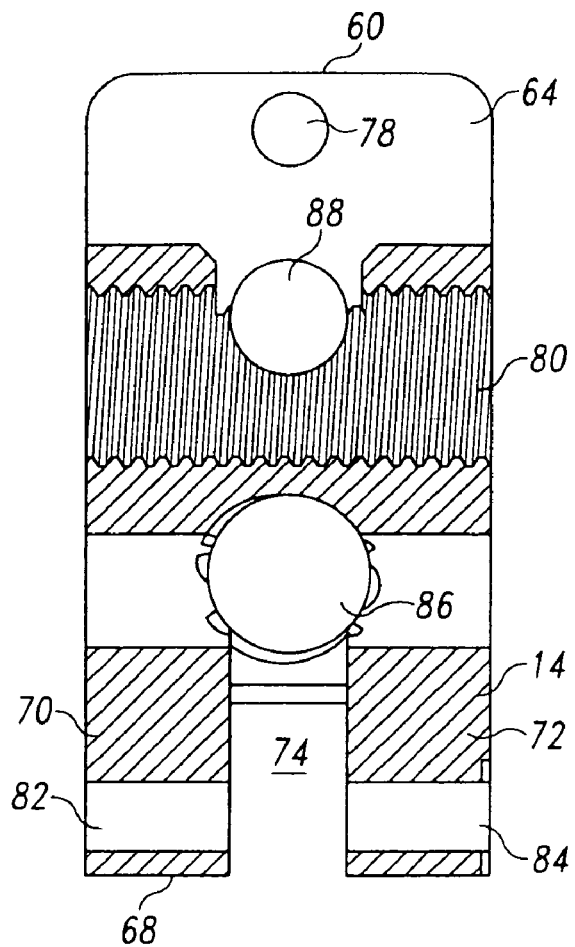
FIG. 5E is a cross-section of the transition block of FIGS. 5A-5D, taken along line 5E-5E of FIGS. 5A and 5C.

As shown in FIG. 5E, the transition block 14 also includes a distal pair of through bores 82, 84 that extend through the walls 70, 72 in a medial-lateral direction. The distal through bores 82, 84 are co-axial and intersect the distal channel 74. A distal threaded through bore 86 extends through the body of the transition block 14 in an anterior-posterior direction. The central portion of the threaded through bore 86 is exposed to the distal channel 74, as shown in FIG. 5D.

The transition block 14 includes additional through bores 88, 90 extending in perpendicular directions, as shown in FIGS. 5B-5E. One of these through bores 88 intersects the proximal threaded bore 80 at a right angle (see FIG. 5E) and the other of these bores 90 intersects the distal threaded bore 86 at a right angle (see FIG. 5D).

Figure 6:
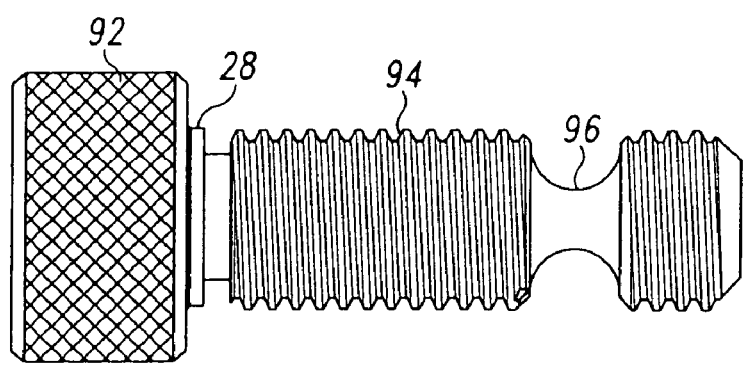
FIG. 6 is an elevation of a representative thumbscrew used in the tibial resection assembly of FIGS. 1-3.

In the tibial resection assembly 10, the proximal threaded bore 80 of the transition block 14 receives the proximal or first thumb screw 28 and the distal threaded bore 86 receives the second thumb screw 30. An example of a suitable structure for both the first and second thumb screws 28, 30 is illustrated in FIG. 6. The thumbscrew of FIG. 6 will be described below as the first thumb screw 28, although it should be understood that this description applies as well to the second thumbscrew 30.

The thumbscrew 28 of FIG. 6 includes a knurled head 92 and an elongate threaded shaft 94 integral with and extending outward from the knurled head 92. The threaded shaft 94 includes an annular, circumferential U-groove 96 about three-fourths of the distance from the head to the opposite end. The annular U-groove 96 in the illustrated embodiment has a radius of curvature of 0.076 inches, although it should be understood that this dimension is provided as an example only; the invention is not limited to any particular dimension unless expressly called for in the claims. The illustrated thumbscrew 28 has a diameter of $5/16^{th}$ inch and fine thread (24 threads per inch in the illustrated embodiment). It should also be understood that the thread characteristics can be varied and that the present invention is not limited to any particular thread characteristic unless expressly called for in the claims. The thread characteristics will to some extent control the degree of fine adjustment available with the resection assembly 10, and the characteristics may be selected to provide the desired degree of adjustment. In the following description, the knurled head, elongated threaded shaft and circumferential U-groove of the second thumbscrew will be referred to as 92', 94' and 96'.

Figure 7:
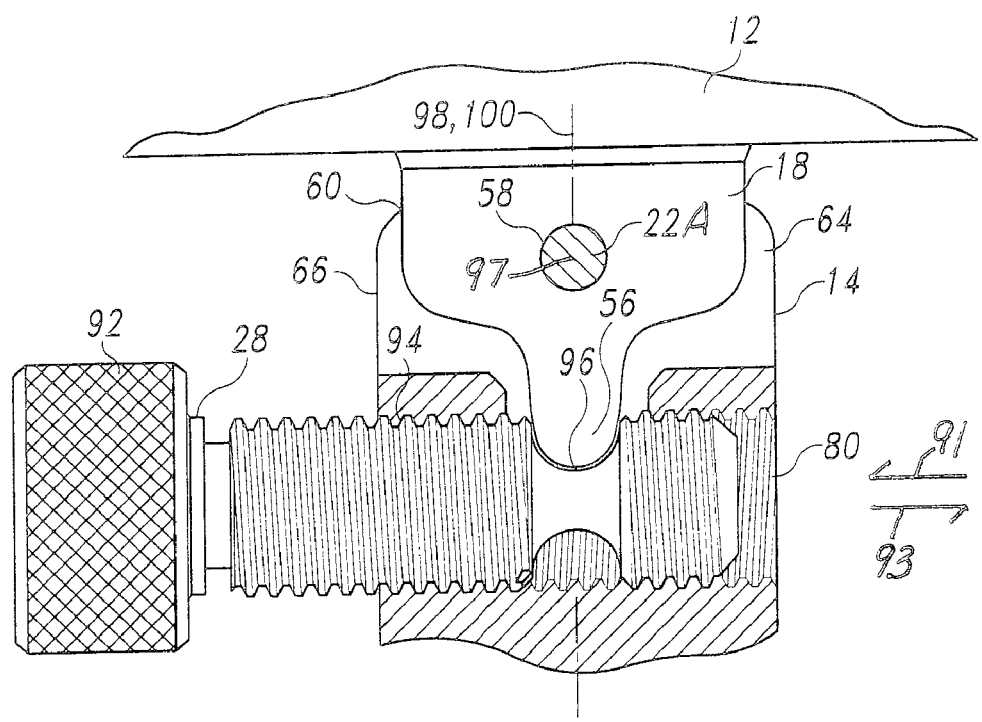
FIG. 7 is a partial cross-section, showing one of the thumbscrews received in a channel of the transition block, with the tang of the varus-valgus adjustment plate received in a U-groove in the thumbscrew, showing the assembly in a neutral varus-valgus orientation.
Figure 8:
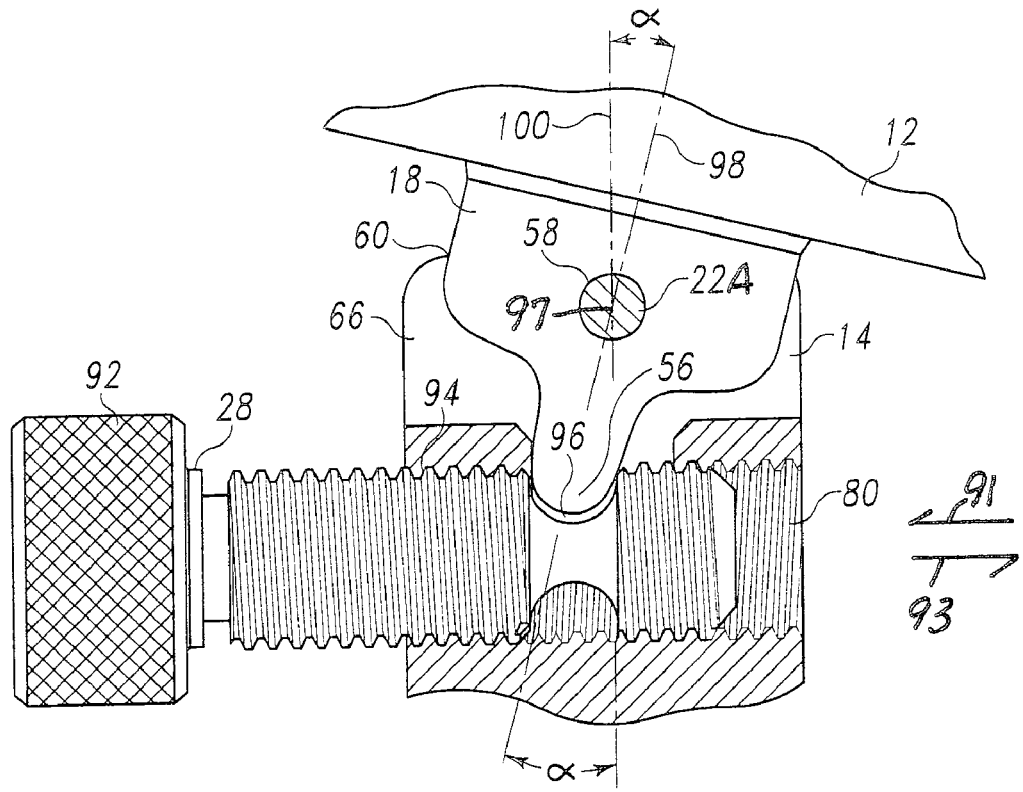
FIG. 8 is a view similar to FIG. 7, showing the assembly in an angled orientation.
Figure 9:
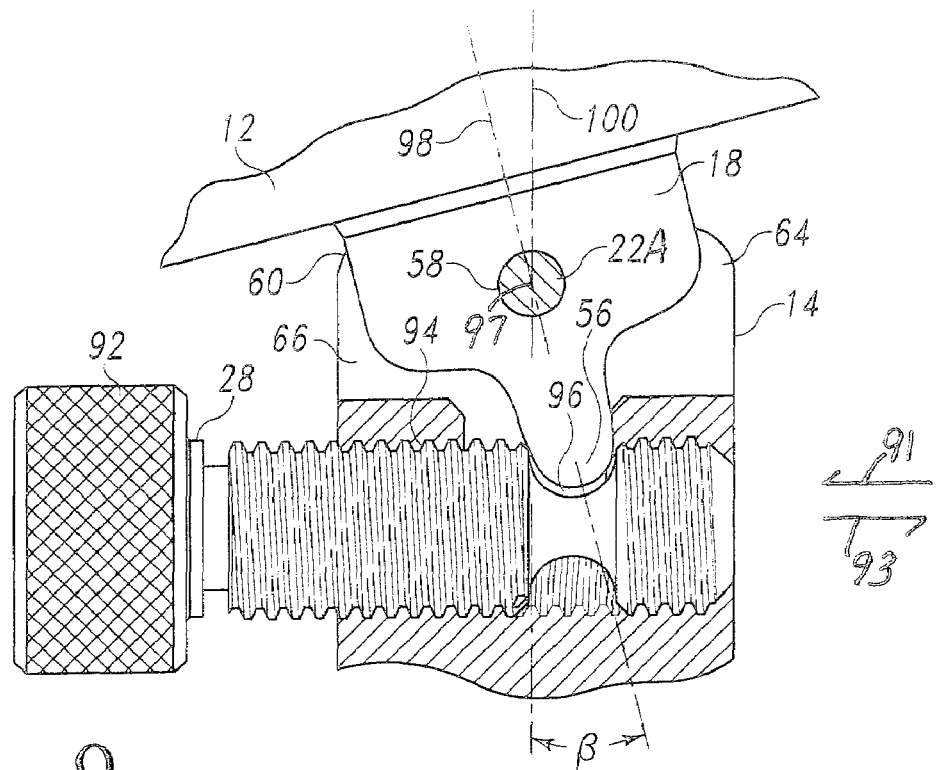
FIG. 9 is a view similar to FIGS. 7 and 8, showing the assembly in a second angled orientation.

In the tibial resection assembly 10, the threaded shaft 94 of the first thumbscrew 28 extends through the proximal threaded bore 80 of the transition block 14 in a medial-lateral direction and is capable of linear translational movement with respect to the transition block in the medial and lateral directions, as indicated by the arrows labeled 91 and 93 in FIGS. 3, 7-9 and 17. As shown in FIGS. 7-9, a portion of the varus-valgus adjustment plate 18 extends into the proximal channel 66 of the transition block 14 and the distal tang 56 of the varus-valgus adjustment plate 18 is received in the U-groove 96 of the first thumbscrew 28. The dowel 22A that extends through the bore 58 of the varus-valgus adjustment plate 18 also extends through the aligned bores 76, 78 of the transition block 14. The varus-valgus adjustment plate 18 can pivot on the dowel 22A, either directly, or the dowel 22A can pivot in the bores 76, 78 of the transition block 14. In either case, the central longitudinal axis of the dowel 22A defines the axis 97 about which the varus-valgus adjustment plate 18 and cutting block 12 can pivot. This axis 97 extends in an anterior-posterior direction, as shown in FIGS. 3, 7-9 and 16.

When the first thumbscrew 28 is turned, the elongate shaft 34 translates in either the medial direction 91 or lateral direction 93 and the medial-lateral position of the U-groove 96 changes. As the position of the U-groove 96 moves either medially or laterally, the distal tang 56 of the varus-valgus adjustment plate 18 also moves since the distal tang 56 is received in the groove 96. Since the varus-valgus adjustment plate 18 is pivotally mounted to the transition block 14 through the dowel 22A, the pivotal movement of the distal tang 56 results in the varus-valgus adjustment plate 18 and the cutting block 12 pivoting about the axis 97 in the varus and valgus directions. FIG. 7 illustrates a neutral position of the varus-valgus adjustment plate 18 and the first thumbscrew 28; in this position, the central longitudinal axis 98 of the varus-valgus adjustment plate 18 is coincident with the central longitudinal axis 100 of the transition block 14. FIG. 8 illustrates an angled orientation of the varus-valgus adjustment plate 18 with respect to the first thumbscrew 28 and transition block 14; in this orientation, the central longitudinal axis 98 defines an angle α with the central longitudinal axis 100 of the transition block 14. FIG. 9 illustrates a second angled orientation of the varus-valgus adjustment plate 18 with respect to the first thumbscrew 28 and transition block 14; in this orientation, the central longitudinal axis 98 defines an angle β with the central longitudinal axis 100 of the transition block 14. Since the plane of the flat proximal cutting guide surface 34 is constantly perpendicular to the central longitudinal axis 98 of the varus-valgus adjustment plate 18, turning the thumbscrew 28 allows the user to adjust the orientation of the varus-valgus adjustment plate 18 by angles of α and β. The characteristics of the threads of the thumbscrew 28 and threaded bore 80 determine the number of angular orientations that can be selected. Generally, in the illustrated embodiment, the user can select any angle between the neutral position and plus or minus 10° from the central longitudinal axis 100 of the transition block 14.

When the desired varus-valgus angle is reached, no locking mechanism is needed: the interaction of the threads of the thumbscrew 28 and threads of the threaded bore 80 will hold the cutting block 12 at the desired angle until the surgeon is ready to fix the cutting block to the patient's bone.

Figures 10A, 10B:
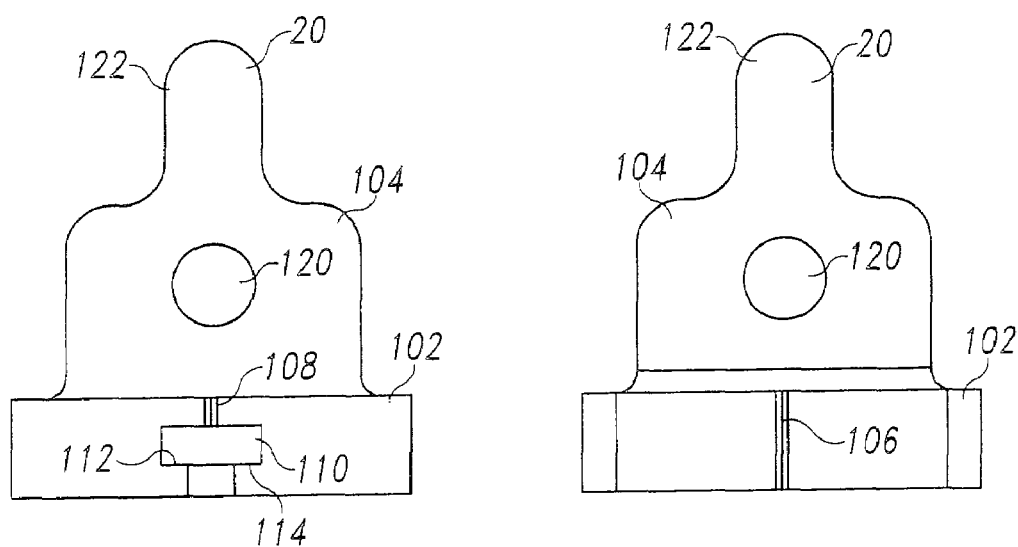
FIG. 10A is a side elevation of the posterior slope adjustment plate of the tibial resection assembly of FIGS. 1-3.
FIG. 10B is a second side elevation of the posterior slope adjustment plate of FIG. 10A.
Figure 10C:
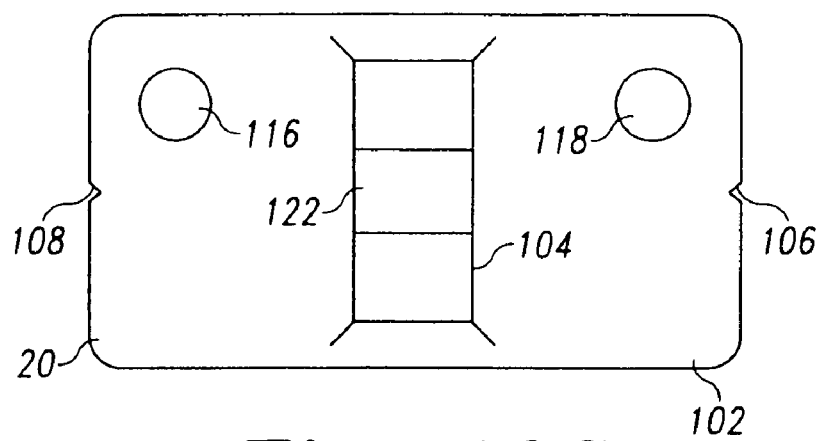
FIG. 10C is a top plan view of the posterior slope adjustment plate of FIGS. 10A-10B.
Figure 10D:
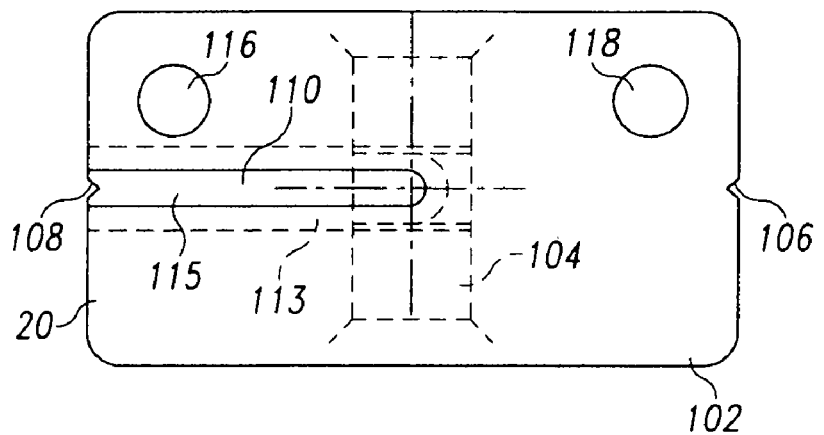
FIG. 10D is a bottom plan view of the posterior slope adjustment plate of FIGS. 10A-10C.
Figure 10E:
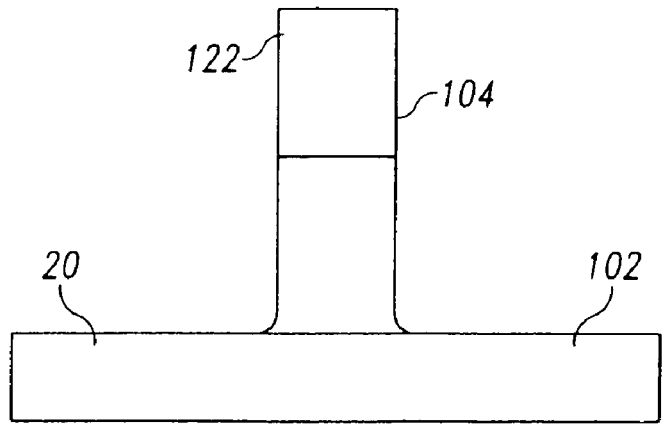
FIG. 10E is a front elevation of the posterior slope adjustment plate of FIGS. 10A-10D.

The transition block 14 is connected in a similar manner to the posterior slope adjustment plate 20. The posterior slope adjustment plate 20 is shown in FIGS. 10A-10E. As there shown, the plate 20 includes a base 102 and a body 104. The base 102 includes a V-groove 106 on the medial side and a second V-groove 108 on the lateral side. The lateral side also includes a T-slot 110 with internal ledges 112, 114. The T-slot 110 has a proximal portion 113 with an enlarged width and a distal portion 115 with a reduced width. The T-slot 10 is open to the distal side of the posterior slope adjustment plate 20. As shown in FIGS. 10C and 10D, the base 102 of the posterior slope adjustment plate 20 has a pair of spaced through bores 116, 118. The body 104 of the posterior slope adjustment plate 20 has a through bore 120 and a proximal tang 122.

Figure 11:
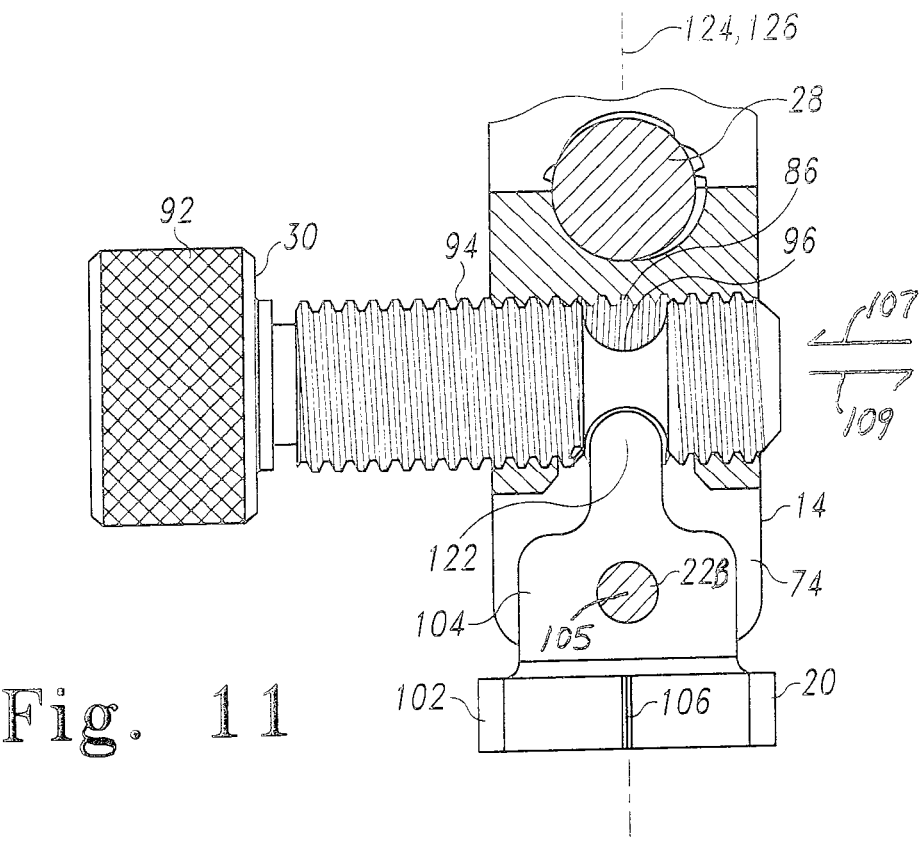
FIG. 11 is a partial cross-section, showing another one of the thumbscrews received in a channel of the transition block, with the tang of the posterior slope adjustment plate received in a U-groove in the thumbscrew, showing the assembly in a neutral orientation.
Figure 12:
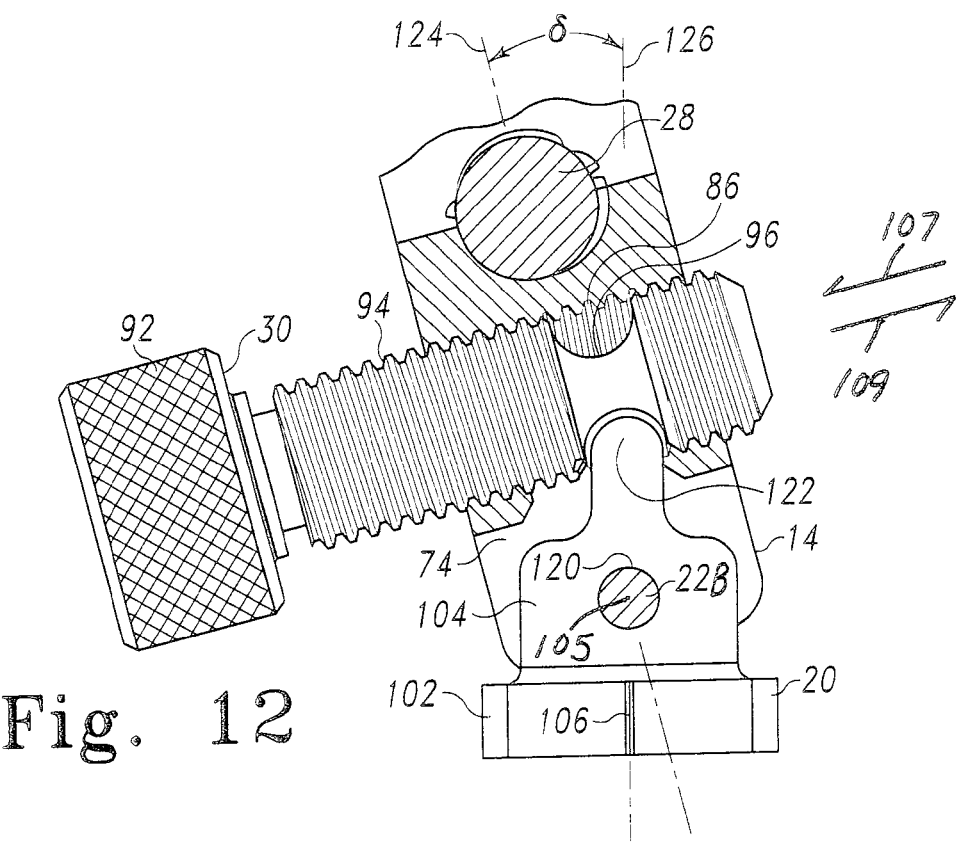
FIG. 12 is a view similar to FIG. 11, showing the assembly in a second angular orientation.

In the tibial resection assembly 10, a portion 103 of the body 104 of the posterior slope adjustment plate 20 extends into the distal channel 74 of the transition block 14 and the threaded shaft 94' of the second thumbscrew 30 extends through the distal threaded bore 86 of the transition block 14 in an anterior-posterior direction and is capable of linear translational movement with respect to the transition block in the anterior and posterior directions, as indicated by the arrows labeled 107 and 109 in FIGS. 3, 11-12, 16 and 18. The proximal tang 122 of the posterior slope adjustment plate 20 is received in the U-groove 96' of the second thumbscrew 30, as shown in FIGS. 11 and 12. A dowel 22B that extends through the bore 120 of the body 104 of the posterior slope adjustment plate 20 also extends through the aligned bores 82, 84 of the transition block 14. The posterior slope adjustment plate 20 can pivot on the dowel 22B, either directly, or the dowel 22B can pivot in the bores 82, 84 of the transition block 14. In either case, the central longitudinal axis of the dowel 22B defines the axis 105 about which the posterior slope adjustment plate 18 can pivot. This axis 105 extends in a medial-lateral direction, as shown in FIGS. 3, 11-12 and 16.

When the second thumbscrew 30 is turned, the elongate shaft 34' translates in either the anterior direction 107 or posterior direction 109 and the anterior-posterior position of the U-groove 96' changes. As the position of the U-groove moves either anteriorly or posteriorly, the proximal tang 122 of the posterior slope adjustment plate 20 also moves. Since the posterior slope adjustment plate 20 is pivotally mounted to the transition block 14 through the dowel 22B, there is relative pivotal movement between the proximal tang 122 of the posterior slope adjustment plate 20 and the transition block 14. Here, this relative pivotal movement results in the transition block pivoting about the medial-lateral axis 105. FIG. 11 illustrates a neutral position of the transition block 14, posterior slope adjustment plate 20 and the second thumbscrew 30; in this position, the central longitudinal axis 124 of the posterior slope adjustment plate 20 is coincident with the central longitudinal axis 126 of the transition block 14. FIG. 12 illustrates an angled orientation of the posterior slope adjustment plate 20 with respect to the second thumbscrew 30 and transition block 14; in this orientation, the central longitudinal axis 124 of the plate 20 defines an angle δ with the central longitudinal axis 126 of the transition block 14.

The angle δ is the posterior slope of the cutting guide surface 34 of the cutting block 12. Since the plane of the flat proximal cutting guide surface 34 is constantly perpendicular to the central longitudinal axis 98 of the varus-valgus adjustment plate 18, and since the varus-valgus adjustment plate 18 is not pivotable in a sagittal plane (about a medial-lateral axis) with respect to the transition block 14, turning the thumbscrew 30 allows the user to adjust the anterior-posterior orientation of the transition block 14 and therefore the anterior-posterior orientation of the cutting guide surface 34. The characteristics of the threads of the thumbscrew 30 and threaded bore 86 determine the number of angular orientations that can be selected. Generally, in the illustrated embodiment, the user can select any angle between the neutral position and plus or minus 10°. It should be understood that although the drawings do not include any illustration of adjustment of the cutting block to provide an anterior slope, such an adjustment is possible, although the foreseeable use will be to set a posterior slope or neutral slope for the proximal tibial resection.

When the desired posterior slope is reached, no locking mechanism is needed: the interaction of the threads of the thumbscrew 30 and threads of the threaded bore 86 will hold the cutting block 12 at the desired angle until the surgeon is ready to fix the cutting block to the patient's bone.

The posterior slope adjustment plate 20 is connected to a pair of dowel rods or pins 22C, 22D through the through bores 116, 118 in the base 102 of the plate 20. These dowel pins 22C, 22D extend to and connect the posterior slope adjustment plate 20 to the pin block 16 as described in more detail below and prevent relative rotation between these components. The posterior slope adjustment plate 20 also receives a portion of the adjustment rod 26 as described in more detail below.

Figure 13A:
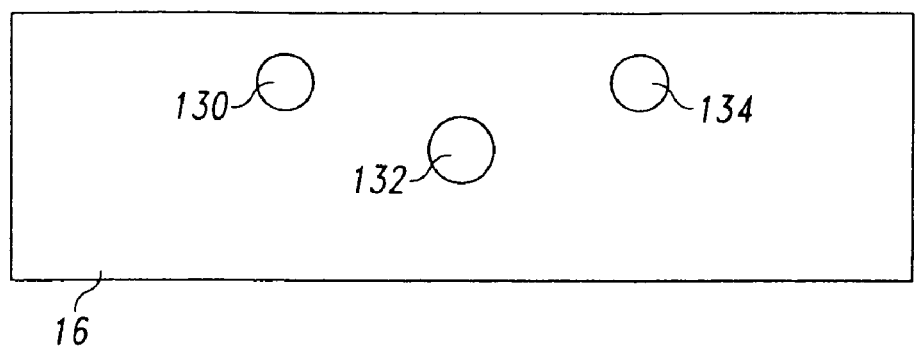
FIG. 13A is a top plan view of the pin block of the tibial resection assembly of FIGS. 1-3, showing the proximal side of the pin block.
Figure 13B:
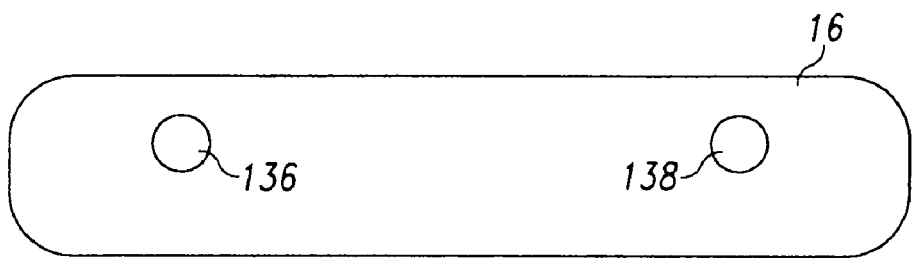
FIG. 13B is an elevation of the anterior side of the pin block of FIG. 13A.

The pin block 16 is illustrated in FIGS. 13A-13B. The illustrated pin block 16 comprises a body with a plurality of through bores. Three through bores 130, 132, 134 shown in FIG. 13A, extend in a proximal-distal direction. Two through bores 136, 138 extend in an anterior-posterior direction, as shown in FIG. 13B. Two of the proximal-distal through bores 130, 134 receive portions of the two dowel pins 22C, 22D that extend to the posterior slope adjustment plate 20. These dowel pins 22C, 22D can slide in the bores 130, 134 to allow relative proximal distal movement between the pin block 16 and the posterior slope adjustment plate 20. The central proximal-distal through bore 132 is threaded. The two anterior-posterior through bores 136, 138 are provided to receive pins intraoperatively to set the preliminary position of the pin block 16 on the patient's tibia.

Figure 14A:
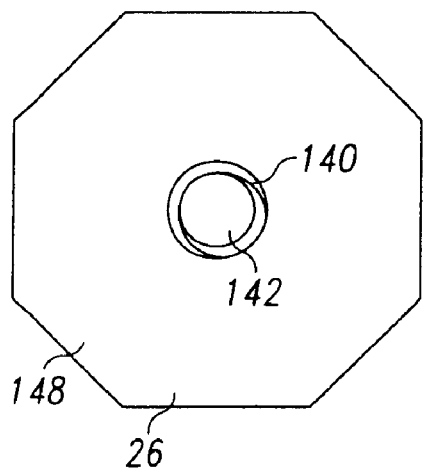
FIG. 14A is an end view of the adjustment rod of the tibial resection assembly of FIGS. 1-3.
Figure 14B:
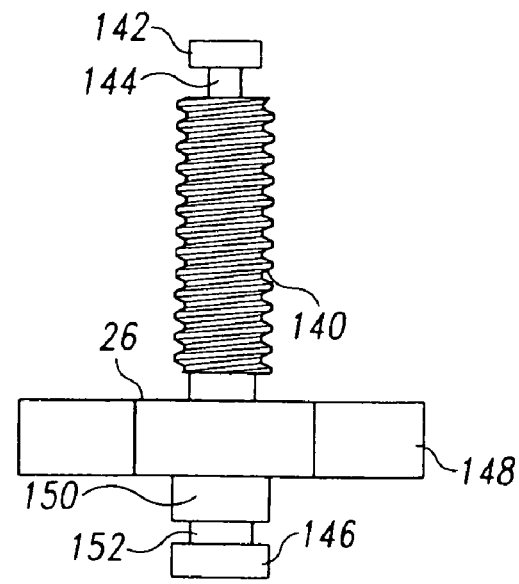
FIG. 14B is a side view of the adjustment rod of FIG. 14A.

The threaded central proximal-distal bore 132 of the pin block 16 receives a threaded shaft 140 of the adjustment rod 26. The adjustment rod 26 is illustrated in FIGS. 14A-14B. At its proximal end, the adjustment rod 26 has a cylindrical proximal mounting flange 142 connected to the threaded shaft 140 through a reduced diameter neck 144. At its distal end, the adjustment rod 26 has a cylindrical distal mounting flange 146. Between the distal mounting flange 146 and the threaded portion 140, the adjustment rod 26 has an enlarged diameter head 148. A neck 150 connects the distal mounting flange 146 and the head 148. The neck 150 includes a reduced diameter portion 152 adjacent to the distal mounting flange 146. The proximal mounting flange 142, proximal neck 144, threaded shaft 140, head 148, distal neck 150 and distal mounting flange 146 are all co-axial.

In the tibial resection assembly 10, the proximal end of the adjustment rod 26 is connected to the posterior slope adjustment plate 20. For this connection, the proximal mounting flange 142 and proximal neck 144 of the adjustment rod 26 are received within the slot 108 (see FIGS. 10A and 10D) of the posterior slope adjustment plate 20. The proximal mounting flange 142 is received within the portion 113 of the T-slot 110 with the enlarged width and the neck 144 is received in the portion 115 of the T-slot 110 with the reduced width. Portions 113 and 115 of the T-slot are illustrated in FIG. 10D.

The threaded shaft 140 of the adjustment rod 26 extends through and engages the threads of the bore 132 of the pin block 16. Thus, by turning the adjustment rod 26, the proximal-distal distance between the pin block 16 and the posterior slope adjustment plate 20 can be adjusted. The threaded connection between the adjustment rod 26 and pin block 16 allow for controlled, fine adjustment of the proximal-distal position of the posterior slope adjustment plate 20, and thereby also allows for controlled, fine adjustment of the proximal-distal position of the transition block 14 and the cutting block 12, including its cutting guide surface 34.

The distal mounting flange 146 of the adjustment rod 26 may be connected to a receiving T-slot formed in the alignment rod 24. FIGS. 15A, 15B and 15C illustrate the features of the alignment rod 24. The rod 24 includes a cylindrical head 160 and a shaft 162. The head 160 includes a receiving T-slot 164 that is sized and shaped to receive the distal mounting flange 146 of the adjustment rod 26; T-slot 164 has a distal portion 166 with an enlarged width and a proximal portion 168 with a reduced width. The T-slot 164 is open to the anterior side of the head 160.

As shown in cross-section in FIG. 15C, the shaft 162 of the alignment rod 24 has an anterior flat surface 170. The shaft 162 of the alignment rod 24 is sized and shaped to be capable of being received within a hollow tube that is connected to an ankle clamp. When so connected, the shaft 162 will be able to telescope in and out of the hollow tube without rotating.

The components 12, 14, 16, 18, 20, 22A, 22B, 22C, 22D, 24, 26, 28 and 30 can be assembled as described above. Grooves (such as grooves 44, 106, 108) or reference marks can be placed on adjacent components to provide a quick visual indication of whether the components are in a neutral position. However, it should be understood that these reference features are not necessary to successfully practice the invention.

A method of using the illustrated tibial resection assembly 10 in surgery is described below.

The patient is placed supine on the operating table and given a satisfactory anesthetic. The leg is prepped and draped in the usual fashion. A standard ankle or malleolar clamp, such as one available with DePuy Orthopaedics' Specialist® 2 instrument system, can be placed on the patient's ankle and the shaft 162 of the alignment rod 24 placed in an alignment tube connected to the ankle clamp, thus mounting the tibial resection assembly 10 to the ankle clamp.

The surgeon can then preliminarily align the resection assembly 10 in a standard manner. For example, the surgeon can visually determine the desired level of tibial resection and set a drill bit, pin or other anchoring member into the patient's bone at this level and in line with the lateral border of the medial femoral condyle. Once this first bit or pin is placed, the surgeon can use it as a reference point. The anterior-posterior groove 36 of the flat cutting guide surface 34 can be positioned to receive the set bit or pin in the groove 36, thus setting a preliminary proximal-distal position for the cutting guide surface 34. If desired, the surgeon can mount a standard stylus assembly 47 to the cutting block 12 as shown in FIG. 3, and use the stylus in the standard manner to determine the appropriate level for the resection. In setting the preliminary proximal-distal position, the surgeon can move the shaft 162 of the alignment rod 24 into and out of the standard tube and can lock the positions of the two tubes.

In setting the preliminary posterior slope of the cutting guide surface 34 of the cutting block 12, the surgeon can translate the lower assembly (ankle clamp and attachments) in an anterior-posterior direction to align the shaft 162 of the alignment rod 24 parallel to the tibial axis. If a posterior slope is desired, the lower assembly can be advanced anteriorly to set the desired slope. In setting the preliminary varus-valgus orientation of the cutting block 12, the lower assembly (ankle clamp and attachments) can be moved in the medial or lateral direction to pivot the cutting guide surface 34 of the cutting block 12.

Figure 16:
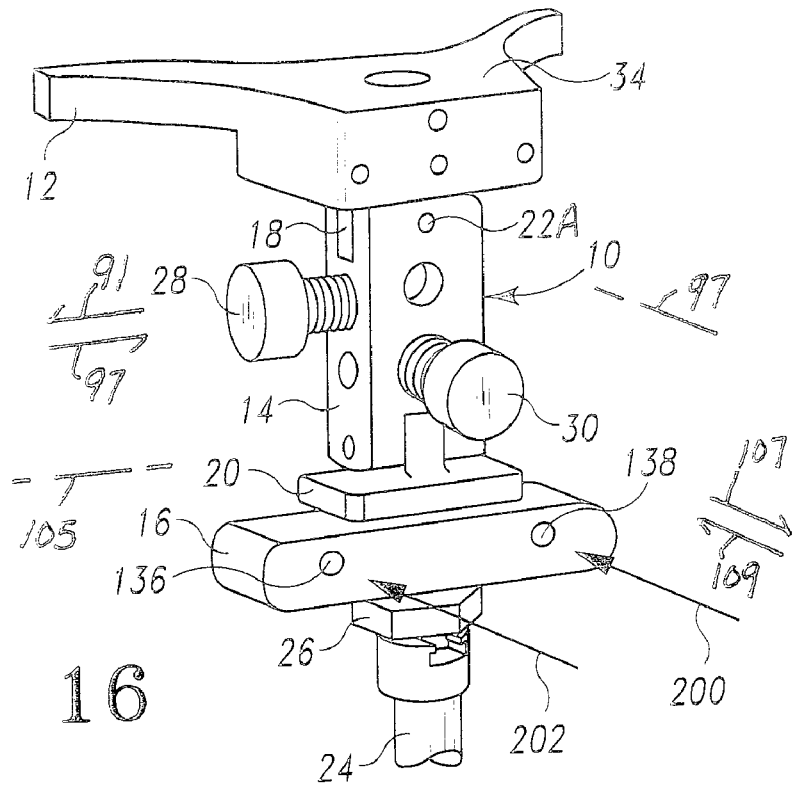
FIG. 16 is a perspective view of the tibial resection assembly of FIGS. 1-3 illustrating the step of setting a preliminary position and orientation of the assembly.

Once the surgeon is satisfied with the preliminary position of the tibial resection assembly 10, the preliminary position can be set by drilling or driving pins or bits through the anterior-posterior through bores 136, 138 of the pin block 16, as shown by arrows 200, 202 in FIG. 16. Once the pins are set into the bone, the position of the pin block 16 is fixed. With the pin block 16 so fixed, the surgeon can then proceed to make fine adjustments to the position and orientation of the cutting guide surface 34 of the cutting block.

Figure 17:
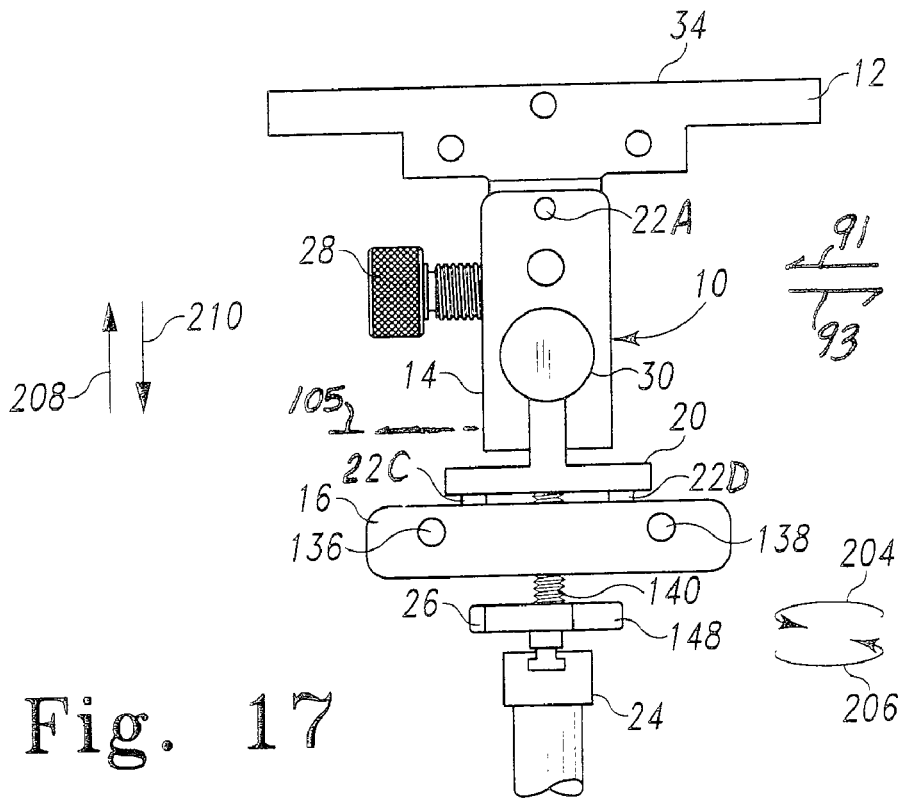
FIG. 17 is a front elevation of the tibial resection assembly of FIGS. 1-3 illustrating the step of adjusting the level of the cutting block in the proximal-distal direction.

As illustrated in FIG. 17, to set the final position of the cutting guide surface 34 in the proximal-distal direction, the surgeon may turn the head 148 of the adjustment rod 26 in either a clockwise or counterclockwise direction (as shown by arrows 204, 206) to rotate the threaded shaft 140 of the adjustment rod in the threaded bore 132 of the pin block 16. As the threaded shaft 140 rotates in the bore 132, the proximal mounting flange 142 of the adjustment rod 26 moves the posterior slope adjustment plate 20 in a proximal or distal direction, thereby moving the transition block 14 and cutting block 12 in a proximal or distal direction, indicated by arrows 208, 210 in FIGS. 16-19. The surgeon is able to make the proximal-distal adjustment in minute controlled increments, due to the fact that the proximal-distal distance moved is controlled by relative motion between the threaded members 132, 140. No further locking is necessary until all adjustments are completed; the interaction of the threaded members 132, 140 maintains the proximal-distal position of the cutting guide surface 34 until the surgeon makes further adjustment by turning the head 148 of the adjustment rod 26. The illustrated tibial resection assembly 10 allows for controlled, fine adjustment of the proximal-distal level of the resection by over 0.2 inches.

Figure 18:
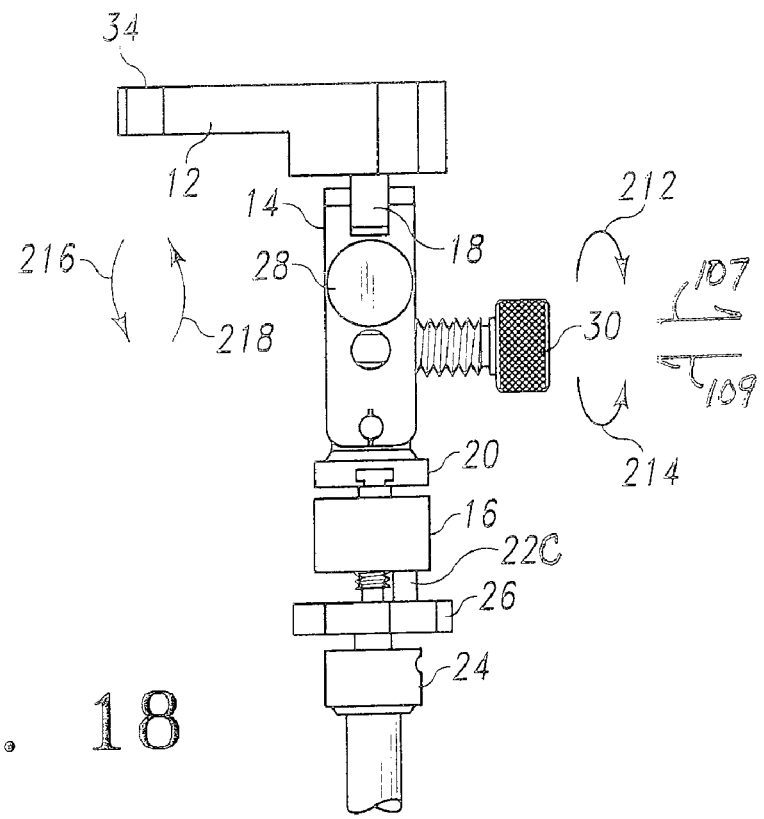
FIG. 18 is a side elevation of the tibial resection assembly of FIGS. 1-3 illustrating the step of adjusting the posterior slope of the cutting block.

As illustrated in FIG. 18, to set the final posterior slope of the cutting guide surface 34 of the cutting block 12, the second thumbscrew 30 is turned in either a clockwise or counterclockwise direction, indicated by arrows 212, 214. As the thumbscrew 30 is rotated, the anterior-posterior position of the U-groove 96' changes, causing relative pivoting between the posterior slope adjustment plate 20 and the transition block 14 about the medial-lateral axis 105 provided by the dowel 22B. As shown in FIG. 18, this relative pivoting results in the transition block 14 and cutting block 12 pivoting to adjust the posterior slope of the cutting guide surface 34. The directions of pivoting are shown by arrows 216, 218 in FIG. 18. The surgeon can continue to rotate the thumbscrew 30 in either direction to set the precise slope desired for the resection in the anterior-posterior direction. The surgeon is able to make the posterior slope adjustment in minute controlled increments, due to the fact that the angular change is controlled by relative motion between the threaded members 30, 86. No further locking is necessary until all adjustments are completed; the interaction of the threaded members 30, 86 maintains the anterior-posterior orientation of the cutting guide surface 34 until the surgeon makes further adjustment by turning the head 92' of the thumbscrew 30. As indicated above, the illustrated tibial resection assembly 10 allows for controlled, fine adjustment of the posterior slope in a range of about +10° to about −10° from the central longitudinal axis 126 of the posterior slope adjustment plate 20.

Figure 19:
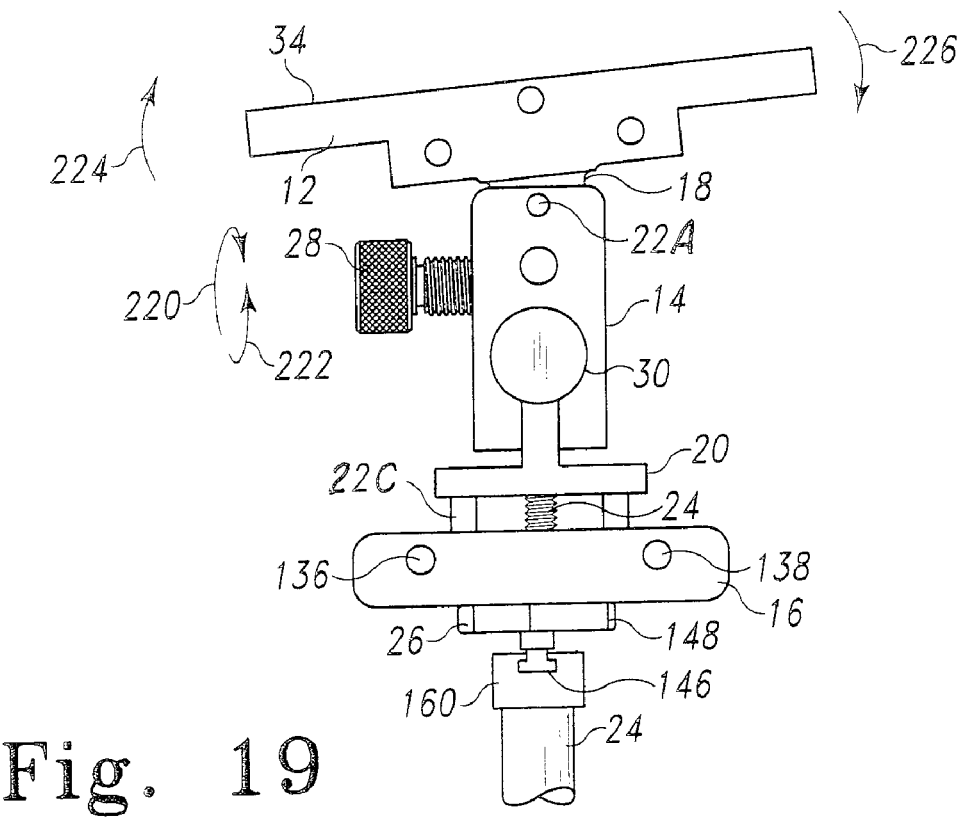
FIG. 19 is a front elevation of the tibial resection assembly of FIGS. 1-3 illustrating the step of adjusting the varus-valgus orientation of the cutting block.

As illustrated in FIG. 19, to set the final varus-valgus slope of the cutting guide surface 34 of the cutting block 12, the first thumbscrew 28 is turned in either a clockwise or counterclockwise direction, indicated by arrows 220, 222. As the thumbscrew 28 is rotated, the medial-lateral position of the U-groove 96 changes, causing relative pivoting between the transition block 14 and the varus-valgus adjustment plate 18 about the generally anterior-posterior axis 97 provided by the dowel 22. As shown in FIG. 19, this relative pivoting results in the cutting block 12 pivoting to provide a medial-lateral slope to the cutting guide surface 34. The directions of pivoting are shown by arrows 224, 226 in FIG. 19. The surgeon can continue to rotate the thumbscrew 28 in either direction to set the precise slope desired for the resection in the medial-lateral direction. The surgeon is able to make the varus-valgus slope adjustment in minute controlled increments, due to the fact that the angular change is controlled by relative motion between the threaded members 28, 80. No further locking is necessary until all adjustments are completed; the interaction of the threaded members 28, 80 maintains the varus-valgus orientation of the cutting guide surface 34 until the surgeon makes further adjustment by turning the head 92 of the thumbscrew 28. As indicated above, the illustrated tibial resection assembly 10 allows for controlled, fine adjustment of the varus-valgus orientation in a range of about +10° to about −10° from the central longitudinal axis 100 of the transition block 14.

Once the surgeon is satisfied with the final position and orientation of the cutting guide surface, pins or bits may be set through the through bores 48, 50 in the cutting block to the underlying bone, thereby fixing the cutting block in its final position and orientation. These pins or bits will stabilize the cutting block 12 during the resection. The tibial plateau may then be resected.

It will be appreciated from the foregoing that the tibial resection assembly 10 of the present invention may be used in conjunction with conventional computer assisted surgical equipment. For example, an emitter or reflector array can be attached to the cutting block 12 or transition block 14 to give the surgeon an image of the position of the cutting guide surface 34 with respect to a desired resection level and orientation as displayed on a computer screen. The fine adjustments can be made to match the position and orientation of the cutting guide surface 34 with the desired position and orientation as displayed on the computer screen.

An example of an emitter or reflector system potentially usable with the present invention is disclosed in U.S. Pat. No. 6,551,325, which is incorporated by reference herein in its entirety. An emitter or reflector stylus could be mounted to the cutting block 12 through the top hole 46 in the cutting block. The resection assembly 10 of the present invention is expected to be particularly useful with the Ci™ computer assisted surgical system available from DePuy Orthopaedics, Inc. of Warsaw, Ind.

All of the components of the tibial resection assembly of the present invention may be made of standard surgical grade material for such instruments, and may be made in conventional ways. For example, surgical grade stainless steel could be used. Dimensions of the components and tolerances can be adjusted to reduce the potential for undesirable play or wobble between components. The increments of the angles can be modified by using finer threads and adjusting the locations of the pivot points provided by the dowels.

While only a specific embodiment of the invention has been described and shown, it is apparent that various alternatives and modifications can be made thereto. Those skilled in the art will also recognize that certain additions can be made to the illustrative embodiment. It is, therefore, the intention in the appended claims to cover all such alternatives, modifications and additions as may fall within the true scope of the invention.

We claim:

1. A finely-adjustable resection guide assembly comprising:
    a first body;
    a second body having anterior and posterior surfaces and a plurality of through-bores extending through the second body from the anterior to the posterior surfaces, the second body being pivotally connected to the first body for relative pivotal movement about a first axis;
    a first threaded member extending through the first body in a first direction and capable of linear translation with respect to the first body in the first direction;
    a second threaded member extending through the first body in a second direction and capable of linear translation with respect to the first body in the second direction;
    a third threaded member extending through the second body in a third direction and capable of linear translation with respect to the second body in the third direction;
    a cutting block having a cutting guide surface, the cutting block being pivotally connected to the first body, wherein linear translation of the first threaded member causes pivotal movement of the cutting block about a second axis perpendicular to the first direction so that the angular orientation of the cutting block with respect to the first body changes as the first threaded member translates;
    wherein linear translation of the second threaded member causes pivotal movement of the cutting block and the first body about the first axis so that the angular orientation of the cutting block with respect to the second body changes as the second threaded member translates while the angular orientation of the cutting block with respect to the first body remains unchanged by translation of the second threaded member;
wherein linear translation of the third threaded member changes the distance between the second body and the cutting surface of the cutting block.

2. The finely-adjustable resection guide assembly of claim 1 wherein:
the first body comprises a transition block; and
the second body comprises a pin block.

3. The finely-adjustable resection guide assembly of claim 1 further comprising:
a proximal plate extending distally from the cutting block for pivotal connection of the cutting block to the first body; and
a distal plate extending proximally from the second body for pivotal connection of the second body to the first body;
wherein a portion of the proximal plate is received within the first body and a portion of the distal plate is received within the first body.

4. A finely-adjustable resection guide assembly comprising:
a first body comprising a transition block;
a second body comprising a pin block having anterior and posterior surfaces and a plurality of through-bores extending through the second body from the anterior to the posterior surfaces, the second body being pivotally connected to the first body for relative pivotal movement about a first axis;
a first threaded member extending through the first body in a first direction and capable of linear translation with respect to the first body in the first direction;
a second threaded member extending through the first body in a second direction and capable of linear translation with respect to the first body in the second direction;
a third threaded member extending through the second body in a third direction and capable of linear translation with respect to the second body in the third direction;
a cutting block having a cutting guide surface, the cutting block being pivotally connected to the first body, wherein linear translation of the first threaded member causes pivotal movement of the cutting block about a second axis;
a proximal plate extending distally from the cutting block for pivotal connection of the cutting block to the first body;
a distal plate extending proximally from the second body for pivotal connection of the second body to the first body;
wherein linear translation of the second threaded member causes pivotal movement of the cutting block about the first axis;
wherein linear translation of the third threaded member changes the distance between the second body and the cutting surface of the cutting block;
wherein the first body includes spaced proximal end walls defining a proximal channel and spaced distal end walls defining a distal channel, the proximal channel being perpendicular to the distal channel; and
wherein a portion of the proximal plate is received in the proximal channel and a portion of the distal plate is received in the distal channel.

5. The finely-adjustable resection guide assembly of claim 4 further comprising:
a dowel pin pivotally connecting the proximal plate to the first body within the proximal channel; and
a dowel pin pivotally connecting the distal plate to the first body within the distal channel.

6. The finely-adjustable resection guide assembly of claim 5 wherein: the proximal plate includes a distal tang; the distal plate includes a proximal tang; the first threaded member includes a circumferential groove receiving the distal tang of the proximal plate; and the second threaded member includes a circumferential groove receiving the proximal tang of the distal plate.

7. The finely-adjustable resection guide assembly of claim 6 wherein the second body includes a plurality of spaced through-bores aligned parallel to the third threaded member, the resection guide assembly further comprising a plurality of spaced dowels extending from the distal plate, each dowel being received in one of the through-bores of the second body, wherein the second body is capable of linear movement with respect to the dowels.

8. The finely-adjustable resection guide assembly of claim 7 wherein the cutting block is capable of pivotal movement of plus or minus ten degrees about the first axis and about the second axis.

9. The finely-adjustable resection guide assembly of claim 8 further comprising an alignment rod connected to the third threaded member.

10. A finely-adjustable tibial resection assembly comprising:
a cutting block having a cutting guide surface;
a varus-valgus adjustment plate extending distally from the cutting block, the varus-valgus adjustment plate having a distal tang;
a transition block having:
spaced proximal end walls defining a proximal channel and spaced distal end walls defining a distal channel, the proximal channel extending in a medial-lateral direction and the distal channel extending in an anterior-posterior direction,
a proximal threaded bore extending in a medial-lateral direction;
a distal threaded bore extending in an anterior-posterior direction;
a proximal screw extending through the proximal threaded bore of the transition block, the proximal screw having a circumferential groove;
a distal screw extending through the distal threaded bore of the transition block, the distal screw having a circumferential groove;
a posterior slope adjustment plate having a proximal tang;
a pin block having a plurality of through bores extending in the proximal-distal direction, at least one of the through bores being threaded, the pin block being positioned distal to the posterior slope adjustment plate;
an adjustment rod having a threaded shaft engaging the threads of the threaded through bore in the pin block, the adjustment rod also including a head and a proximal end in contact with the posterior slope adjustment plate;
wherein the distance between the pin block and the cutting guide surface can be adjusted by turning the head of the adjustment rod; and
wherein: a portion of the varus-valgus plate is received in the proximal channel of the transition block and pivotally connected to the transition block so that the varus-valgus plate and the cutting block are capable of pivoting with respect to the transition block about an anterior-posterior axis; a portion of the posterior slope adjustment plate is received in the distal channel of the transition block and pivotally connected to the transition block so that the posterior slope adjustment plate is capable of pivoting with respect to the transition block about a medial-lateral axis; the distal tang of the varus-valgus plate is received in the circumferential groove of the proximal screw; and the proximal tang of the posterior slope adjustment plate is received in the circumferential groove of the distal screw.

11. The finely-adjustable tibial resection assembly of claim 10 wherein the posterior slope of the cutting guide surface is adjustable plus or minus ten degrees from a proximal-distal axis of the transition block.

12. The finely-adjustable tibial resection assembly of claim 10 wherein the varus-valgus orientation of the cutting guide surface is adjustable plus or minus ten degrees from an anterior-posterior axis of the transition block.

13. The finely-adjustable tibial resection assembly of claim 10 wherein the pin block has an anterior surface, a posterior surface and a plurality of through-bores extending from the anterior to the posterior surface.

14. The finely-adjustable tibial resection assembly of claim 10 wherein the adjustment rod has a distal end, the assembly further comprising an alignment rod extending in a distal direction from the distal end of the adjustment rod.

* * * * *